United States Patent [19]

Medow et al.

[11] 3,943,251

[45] Mar. 9, 1976

[54] OPHTHAMOLOGICAL USE OF HYDRASTIS COMPOUNDS

[76] Inventors: Norman B. Medow, 18 Sheridan Road, Scarsdale, N.Y. 10583; Joseph J. Greco, 68 Alderbrook Road, Topsfield, Mass. 01983

[22] Filed: Jan. 27, 1975

[21] Appl. No.: 544,044

Related U.S. Application Data

[62] Division of Ser. No. 373,996, June 6, 1973, Pat. No. 3,903,282.

[52] U.S. Cl. .............................................. 424/258
[51] Int. Cl.$^2$......................................... A61K 31/47
[58] Field of Search ................................... 424/258

[56] References Cited
OTHER PUBLICATIONS
Lieb et al., Chem. Abst., Vol. 54, (1960) p. 11271g.

*Primary Examiner*—Jerome D. Goldberg
*Assistant Examiner*—Allen J. Robinson

[57] ABSTRACT

Topical application of hydrastis compounds, such as hydrastine, berberine and canadine, or salts thereof alone or in ophthalmic solutions for the purposes of dilating the pupil, topical anesthesia and/or fluorescently staining (temporarily) of corneal epithelial defects and/or fluorescence in applanation tonometry.

7 Claims, No Drawings

OPHTHAMOLOGICAL USE OF HYDRASTIS COMPOUNDS

This application is a division of application Ser. No. 373996, filed June 6, 1973, now U.S. Pat. No. 3,903,282 issued 9/2/75.

This invention relates to ophthalmology. It more particularly refers to a new method of assisting in ophthalmological observation and analysis.

The hydrastis family of alkaloids has been known for a very long time. Typical members of this family include hydrastine, berberine and canadine. This family of compounds, particularly berberine has been fairly widely used in the past as an anti-asthmatic and anti-bronchial spasmatic. In this use, it has been administered orally and intravenously. No evidence has been found of the intentional topical application of hydrastis type compounds for any medicinal or pharmacological purpose. There have been reports that compounds of this type are lethal in moderately large doses. There is also evidence to support an observation by one reporter that death caused by moderately large oral ingestion of a hydrastis compound was accompanied by dilation of the deceased's eyes.

It has now been found that hydrastic compounds can be used to serve a very valuable function in opthalmological investigation, diagnosis and treatment. These compounds can be applied topically to the eye in rather small dosages. When used in solution, in the preferred manner, the hydrastis compound or a physiologically unobjectionable salt thereof can be admixed with other materials such as thickening and/or lubricating agents, e.g. methycellulose and/or benzal konium chloride. When applied topically in the eye as an aqueous solution, the hydrastis compound should constitute about a ¼ to 10% solution. Application is per drop, one to two drops per instillation. The hydrastis compound or salt thereof, with or without an appropriate solvent and/or other materials, is suitably applied directly to the eye with a conventional eye dropper. There is a dilation of the pupil which will remain in a dilated condition for up to about ten days. There are two other effects which have been found to be of great assistance in examination work. The topical application of hydrastis compounds stains corneal opithelial defects a fluorescent yellow green, thereby making their observation possible and practical under a cobalt blue light. Additionally, hydrastis compounds topically applied selectively anesthetize the cornea and paralyze the sphincter muscle of the iris and the ciliary body muscle. Still further, additional benefits of the use of this family of compounds in this application is that they have been found to possess antibiotic, antiviral, anti-protozoal, and anti-fungal properties in their topical environment. The fluorescence produced is useful in applanation tonometry.

The following Examples will serve to illustrate this invention without being limiting thereon. Parts and percentages are on a solution % basis unless specified to the contrary.

Examples 1 and 2

Solution of berberine of ½% and 1% in methyl cellulose were prepared and topically applied to the patient's eyes in a dosage of 3 drops per patient. It was found that the pupils of the patient's eyes dilated and that their ciliary muscles were temporarily paralyzed and the cornea anesthesized.

Examples 3 and 4

Berberine sulfate was topically applies to a patient's eyes in a solution strength of ¼% and 2% to a total dosage of 3 drops per patient. The patient's pupils dilate.

Example 5

Example 3 was repeated adding 10% methyl cellulose to the preparation. The same results were observed.

Example 6

Example 3 is repeated with hydrastine with the same results.

Example 7

A ½% solution of berberine sulfate in water containing 1% methyl cellulose was topically applied to a patient's eyes to a total dosage of 3 drops per patient. The treated eyes were examined under cobalt blue light and epithelial defects in the cornea showed up very nicely.

What is claimed is:

1. The process of dilating human eye pupils which comprises topically applying a sufficient amount of berberine to effectively dilate said pupils.

2. The process claimed in claim 1 wherein said berberine is applied as a physiologically unobjectionable salt thereof.

3. The process claimed in claim 1 wherein said berberine, or a physiologically unobjectionable salt thereof, is applied as a solution in a substantially inert solvent.

4. The process claimed in claim 3 wherein the solvent is water.

5. The process claimed in claim 3 wherein the concentration is about ¼% to 10% solution.

6. The process claimed in claim 1 wherein the dosage is about ½% to 10% solution.

7. The process claimed in claim 1 including incorporating a buffer and a preservative with said berberine compound.

* * * * *